United States Patent
Bambal et al.

(10) Patent No.: US 7,056,654 B2
(45) Date of Patent: Jun. 6, 2006

(54) SCREENING ASSAY FOR INHIBITORS OF HUMAN CYTOCHROME P-450

(75) Inventors: Ramesh B Bambal, King of Prussia, PA (US); Jacqueline Carol Bloomer, Ware (GB)

(73) Assignees: SmithKline Beecham Corporation, Philadelphia, PA (US); SmithKline Beecham p.l.c., Brentford (GB)

( * ) Notice: Subject to any disclaimer, the term of this patent is extended or adjusted under 35 U.S.C. 154(b) by 325 days.

(21) Appl. No.: 10/149,804

(22) PCT Filed: Dec. 8, 2000

(86) PCT No.: PCT/EP00/12450

§ 371 (c)(1),
(2), (4) Date: Sep. 11, 2002

(87) PCT Pub. No.: WO01/14361

PCT Pub. Date: Mar. 1, 2001

(65) Prior Publication Data

US 2003/0077686 A1    Apr. 24, 2003

Related U.S. Application Data

(60) Provisional application No. 60/170,405, filed on Dec. 13, 1999.

(51) Int. Cl.
*C12Q 1/00* (2006.01)
(52) U.S. Cl. .......................................................... 435/4
(58) Field of Classification Search ................ 435/18, 435/25, 4
See application file for complete search history.

(56) References Cited

U.S. PATENT DOCUMENTS

| 6,420,131 B1 * | 7/2002 | Miller et al. ................... 435/25 |
| 6,617,124 B1 | 9/2003 | Clarke ......................... 435/25 |
| 6,756,209 B1 | 6/2004 | Bambal et al. ................ 435/18 |
| 6,762,034 B1 | 7/2004 | Bloomer et al. ............... 435/25 |
| 2004/0014160 A1 | 1/2004 | Bloomer et al. ............... 435/15 |

FOREIGN PATENT DOCUMENTS

| WO | WO 99/58710 | 11/1999 |
| WO | WO 00/22159 | 4/2000 |
| WO | WO 00/44933 | 8/2000 |
| WO | WO 01/14361 | 3/2001 |
| WO | WO 02/12542 A2 | 2/2002 |

OTHER PUBLICATIONS

Miller, et al., "Flow cytometric techniques for measurement of cytochrome P-450 activity in viable cells.", (1990), Methods in Cell Biology, 33, pp. 71-79.
White, et al., "Characteristics of Rat Hepatocytes Sorted by Fluorescence-Activated Flow Cytometry Effects of Mixed Function Oxidase Inducers", (1989), Biochemical Pharmacology, vol. 38, No. 10, p. 1639-1646.
White, et al., "Fluorescence-Activated Sorting of Rat Hapatocytes Based on Their Mixed Function Oxidase Activities Towards Diethoxyfluorescein", Biochemical Journal, vol. 247, No. 1, pp. 23-28, (1987).

* cited by examiner

*Primary Examiner*—Sandra E. Saucier
(74) *Attorney, Agent, or Firm*—Loretta J. Sauermelch; Mary E. McCarthy; Charles M. Kinzig

(57) ABSTRACT

Fluorescein derivative as a substrate for cytochrome P450 enzymes.

8 Claims, 1 Drawing Sheet

Figure 1: Ketoconazole inhibition of diethoxyfluorescein metabolism by CYP3A4
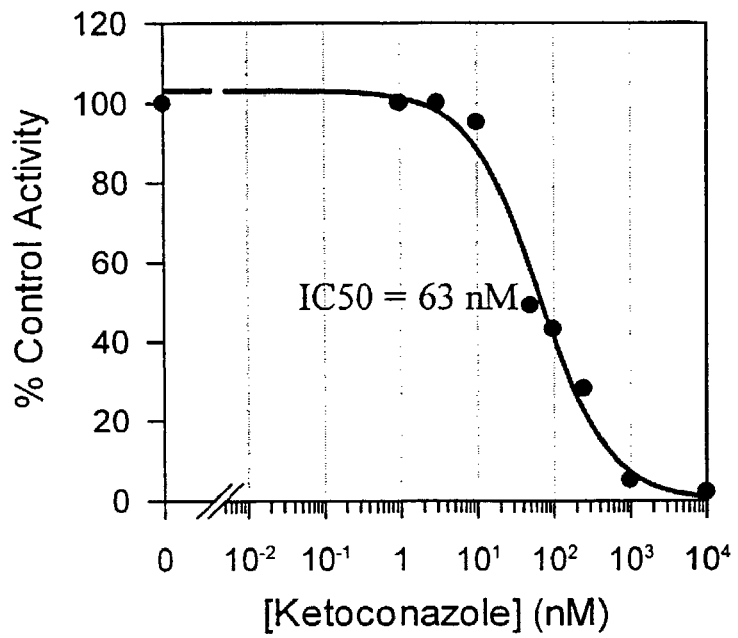
Figure 2: Quercitin inhibition of diethoxyfluorescein metabolism by CYP2C8
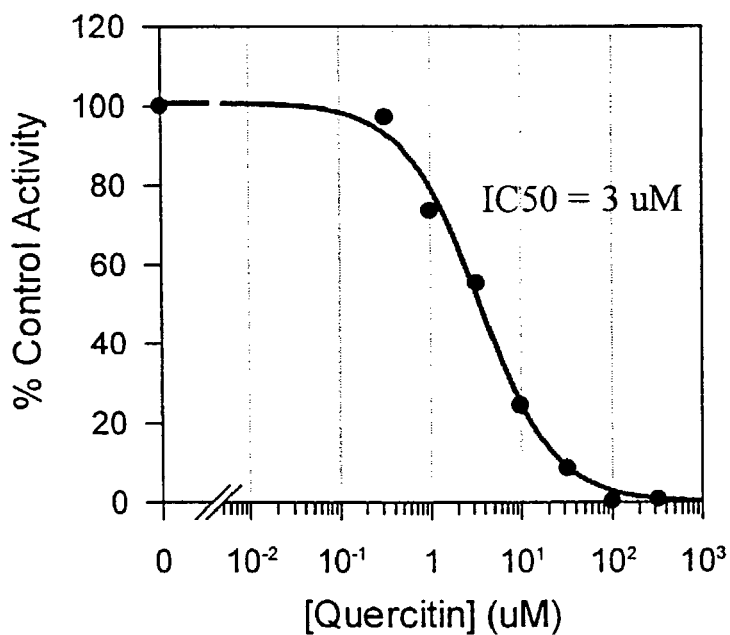

SCREENING ASSAY FOR INHIBITORS OF HUMAN CYTOCHROME P-450

This is a 371 of International Application PCT/EP00/12450, filed Dec. 8, 2000, which claims benefit from the following U.S. Provisional Application: 60/170,405 filed Dec. 13, 1999.

This invention relates to the use of a fluorescein derivative as a substrate for cytochrome P450 enzymes.

The majority of metabolism based drug interactions are a result of inhibition of cytochrome P450 enzymes. Drug interactions involving individual P450 enzymes can be predicted using in vitro methods. Typical in vitro P450 enzyme assays involve incubation of an appropriate substrate with a source of enzyme. Traditionally, time consuming chromatographic methods have been used for metabolite detection in these incubations. More recently the availability of fluorimetric plate readers has facilitated the higher throughput of enzyme assays in general. Adapting P450 assays to fluorescent plate reader technology requires the identification of substrates with appropriate fluorescent products for individual enzymes. Among the xenobiotic-metabolising cytochromes P450, CYP3A4 is one of those commonly responsible for the metabolism of drugs. CYP2C8 has also been identified as being responsible for the metabolism of some drugs.

Resorufin benzyl ether has been described for high throughput CYP3A4 inhibition screening (Crespi et al, *Anal. Biochem.*, 1997, 248, 188–190). However, the rate of resorufin benzyl ether metabolism by CYP3A4 is low, therefore a more appropriate CYP3A4 substrate is required to enable higher throughput inhibition screening. The use of dibenzylfluorescein as a substrate for CYP3A4 and CYP2C8 has also been disclosed, Crespi et al, "Innovative Technologies for the Study of Drug Metabolism", presented at the 7th European ISSX Meeting, Budapest, Hungary, Aug. 22–26, 1999. However this assay has a low signal to noise ratio, therefore, a more appropriate CYP3A4 or CYP2C8 substrate is required to improve the sensitivity for inhibition screening.

Miller, *Anal. Biochem.*, 1983, 133, 46–57 describes the compound diethoxyfluorescein and the investigation of its metabolism by mouse liver homogenates and cultured mouse hepatoma cells. Miller concludes that diethoxyfluorescein is not useful for the detection of inducible mouse cytochromes P450.

WO 00/44933 discloses a resorufin derivative as a CYP3A4 substrate.

Diethoxyfluorescein has now been identified as a general substrate for human cytochrome P450 enzymes. In particular diethoxyfluorescein is an improved substrate for human CYP3A4 and CYP2C8, which is of use for configuring high throughput inhibition screening assays.

According to the invention there is provided an assay for identifying inhibitors of a human cytochrome P450 enzyme which comprises contacting the enzyme and a compound of formula (I):

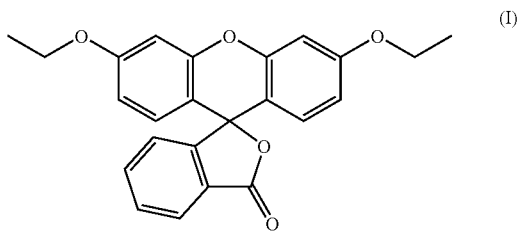

(I)

with a test compound and measuring inhibition of O-dealkylation of the compound of formula (I) by the enzyme.

The human cytochrome P450 enzyme used in the process of the invention is preferably CYP3A4 or CYP2C8, more preferably CYP3A4.

Generally the rate of O-dealkylation of the compound of formula (I) in the absence of test compound will be known, as will the extent of O-dealkylation at given time points. The assay may identify inhibition of O-dealkylation continuously or at specified time points.

O-Dealkylation of the compound of formula (I) following incubation with e.g. CYP3A4 or CYP2C8 gives an O-dealkylated compound which exists in tautomeric forms as shown below:

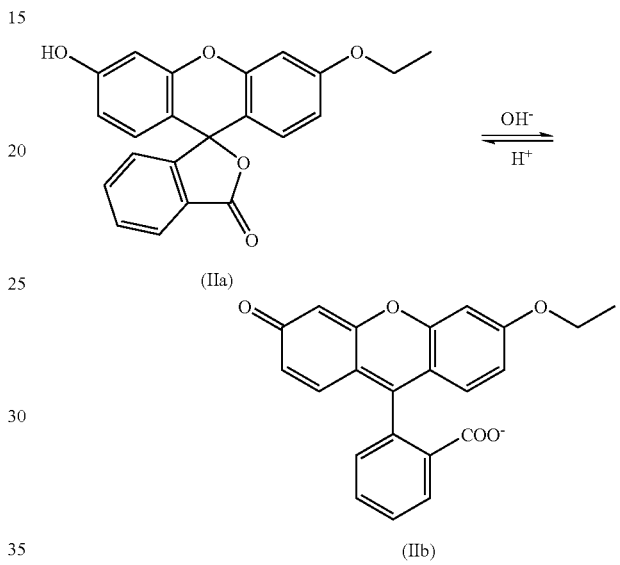

The nonfluorescent lactone (IIa) predominates at low pH whilst the fluorescent charged form (IIb) predominates at neutral to basic pH.

The readily quantifiable fluorescent product of formula (IIb) can be scanned with suitable excitation and emission wavelengths, for example an excitation wavelength of 485 nm and an emission wavelength of 530 nm. Inhibition of O-dealkylation of the compound of formula (I) by the enzyme is preferably measured by quantifying the compound of formula (IIb).

The assay may be carried out either in solution or utilising a solid support in which case the enzyme may be attached to a solid support. When the assay is carried out in solution suitable solvents include methanol and acetonitrile.

The assay is preferably performed in a solution buffered to a pH of 7.4 or 7.5, e.g. using a potassium phosphate or Tris HCl buffer. The assay may also be performed in potassium phosphate buffer containing 10 mM $MgCl_2$. The assay is preferably performed at a temperature of 37° C.

The test compound may be pre-incubated with enzyme prior to the addition of the substrate, or alternatively the substrate may be added simultaneously with the test compound. Final concentrations of enzyme and substrate are calculated so as to achieve a suitable rate of processing for carrying out the assay. If desired, the reaction may be stopped, for example by addition of acid or solvent.

As will be apparent to those skilled in the art cofactors for the human cytochrome P450 enzyme will be present in the assay system, cofactors for human cytochrome P450 enzymes are NADP, glucose-6-phosphate and glucose-6-dehydrogenase. NADH or NADPH may be used instead of NADP. The assay may conveniently be initiated by addition of the cofactor solution, preferably prewarmed to 37° C., to the test compound/enzyme/substrate mixture.

The fluorescent product of formula (II) may be analysed using any conventional system of fluorescence detection, for example a multi-well plate/fluorescent plate reader.

The compound of formula (I) may be prepared according to the procedure described by Miller, *Anal. Biochem.*, 1983, 133, 46–57.

Since the inhibition of cytochrome P450 enzymes is often the mechanism for drug/drug interactions, the assay according to the invention is particularly useful for identifying compounds which may give rise to adverse drug/drug interactions. The assay can therefore be used in combination with the chemical modification of test compounds to increase a test compounds potential for use as a pharmaceutical.

Thus according to further aspects of the invention there are provided a method for reducing the human cytochrome P450 enzyme inhibitory activity of a compound, comprising the steps of identifying the compound as an inhibitor of a human cytochrome P450 enzyme in the assay described above; and thereafter producing a chemically modified version of the test compound in which the functionality suspected to be responsible for the human cytochrome P450 enzyme inhibition is eliminated or changed; and novel compounds produced according to this method.

The chemical modification of test compounds according to this method can be performed using techniques well known to those skilled in the art.

The novel compounds produced according to this aspect of the invention may find application as pharmaceuticals. A compound produced according to this method will be readily identifiable as novel by performing routine literature and database searches. The pharmaceutical activity of such compounds can be readily ascertained using conventional biological screening methods known to those skilled in the art.

All publications, including but not limited to patents and patent applications, cited in this specification are herein incorporated by reference as if each individual publication were specifically and individually indicated to be incorporated by reference herein as though fully set forth.

The invention is illustrated by the following example and figures.

FIG. 1 shows the ketoconazole inhibition of diethoxyfluorescein metabolism by CYP3A4.

FIG. 2 shows the quercitin inhibition of diethoxyfluorescein metabolism by CYP2C8.

EXAMPLE 1

Assay Methodology for CYP3A4

Materials:
500 µM diethoxyfluorescein, (i.e. 0.194 mg/mL in acetonitrile)—store at approx. −20° C. in the dark
2% (w/v) NaHCO$_3$—store at approx. 4° C.
50 mM potassium phosphate buffer, pH 7.4
  Freshly prepared cofactor solution:—approx. the following per mL of 2% (w/v) NaHCO$_3$
  1.7 mg NADP, monosodium salt
  7.8 mg glucose-6-phosphate, monosodium salt
  6 Units glucose-6-phosphate dehydrogenase, Type VII from Bakers Yeast Method:
1) Pre-warm the plate reader oven to 37° C. and pre-warm the lamp for at least 10 minutes.
2) Mix 2.5 µL of 500 µM diethoxyfluorescein, 4 µL (40 µg) CYP3A4 microsomal protein and 213.5 µL buffer per incubate (giving 5 µM diethoxyfluorescein and 160 µg/mL protein final concentration).
3) To each well of a 96-well plate add 220 µL of incubation mix and 5 µL of test compound solution (or 5 µL of appropriate solvent for control wells—methanol or acetonitrile may be used).
4) Pre-incubate the multi-well plate in the plate reader at 37° C. for 5 minutes. Pre-warm the cofactor solution at 37° C. for 5 minutes.
5) Add 25 µL cofactor solution to each well and scan with an excitation wavelength of 485 nm and an emission wavelength of 530 nm with a gain of 80. Scan for 10 cycles at 1 minute intervals.

Results
Confirmation of diethoxyfluorescein as a CYP3A4 substrate was achieved using ketoconazole, a diagnostic CYP3A4 inhibitor (Baldwin et al, *Xenobiotica*, 1995, 25, 261–270). With ketoconazole, diethoxyfluorescein was inhibited with an IC$_{50}$ of 63 nM (FIG. 1), an inhibition value typical of other, well characterised, CYP3A4 substrates.

EXAMPLE 2

Assay Methodology for CYP2C8

Materials:
400 µM diethoxyfluorescein, (i.e. 0.155 mg/mL in acetonitrile)—store at approx. −20° C. in the dark
2% (w/v) NaHCO$_3$—store at approx. 4° C.
50 mM potassium phosphate buffer, pH 7.4
  Freshly prepared cofactor solution:—approx. the following per mL of 2% (w/v) NaHCO$_3$
  1.7 mg NADP, monosodium salt
  7.8 mg glucose-6-phosphate, monosodium salt
  6 Units glucose-6-phosphate dehydrogenase, Type VII from Bakers Yeast Method:
1) Pre-warm the plate reader oven to 37° C. and pre-warm the lamp for at least 10 minutes.
2) Mix 2.5 µL of 400 µM diethoxyfluorescein, 5 µL (50 µg) CYP2C8 microsomal protein and 212.5 µL buffer per incubate (giving 4 µM diethoxyfluorescein and 200 µg/mL protein final concentration).
3) To each well of a 96-well plate add 220 µL of incubation mix and 5 µL of test compound solution (or 5 µL of appropriate solvent for control wells—methanol, DMSO or acetonitrile may be used).
4) Pre-incubate the multi-well plate in the plate reader at 37° C. for 5 minutes. Pre-warm the cofactor solution at 37° C. for 5 minutes.
5) Add 25 µL cofactor solution to each well and scan with an excitation wavelength of 485 nm and an emission wavelength of 530 nm with a gain of 80. Scan for 10 cycles at 1 minute intervals.

Results
Confirmation of diethoxyfluorescein as a CYP2C8 substrate was achieved using quercitin, a CYP2C8 inhibitor (Rahman et al, *Cancer Research*, 1994, 54(1), 5543–5546). With quercitin, diethoxyfluorescein metabolism was inhibited with an IC$_{50}$ of 3 µM (FIG. 2), an inhibition value typical of other, well characterised, CYP2C8 substrates.

The invention claimed is:
1. An assay for identifying inhibitors of a human cytochrome P450 enzyme which comprises contacting the enzyme and a compound of formula (I):

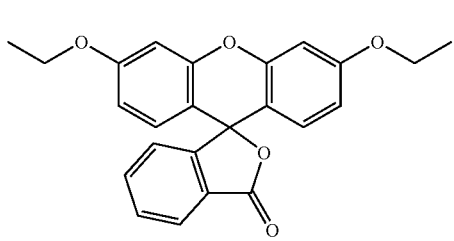

(I)

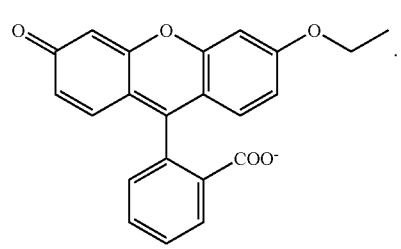

(IIb)

with a test compound and measuring inhibition of O-dealkylation of the compound of formula (I) by the enzyme.

2. The assay according to claim 1 wherein the human cytochrome P450 enzyme is CYP3A4 or CYP2C8.

3. The assay according to claim 2 wherein the human cytochrome P450 enzyme is CYP3A4.

4. The assay according to claim 1 wherein inhibition of O-dealkylation of the compound of formula (I) by the enzyme is measured by quantifying the compound of formula (IIb):

5. The assay according to claim 4 wherein the compound of formula (IIb) is quantified by fluorescence detection.

6. The assay according to claim 5 wherein the compound of formula (IIb) is quantified by scanning at excitation wavelength of 485 nm and an emission wavelength of 530 nm.

7. The assay according to claim 4 wherein the human cytochrome P450 enzyme is CYP3A4 or CYP2C8.

8. The assay according to claim 7 wherein the human cytochrome P450 enzyme is GYP3A4.

* * * * *